United States Patent [19]

Ferenz et al.

[11] Patent Number: 5,374,446
[45] Date of Patent: Dec. 20, 1994

[54] LINKED ESTERIFIED ALKOXYLATED POLYOLS USEFUL AS REDUCED CALORIE FAT SUBSTITUTES

[75] Inventors: Michael R. Ferenz, Coatesville, Pa.; Bernard C. Sekula, High Bridge, N.J.

[73] Assignees: Arco Chemical Technology, L.P., Englewood Cliffs, N.J.; CPC International Inc., Wilmington, Del.

[21] Appl. No.: 165,139

[22] Filed: Dec. 10, 1993

[51] Int. Cl.$^5$ .............................. A23D 9/00
[52] U.S. Cl. .................... 426/611; 426/804; 536/18.3
[58] Field of Search .............. 426/804, 611; 536/18.3

[56] References Cited

U.S. PATENT DOCUMENTS

| | | | |
|---|---|---|---|
| 3,227,595 | 8/1967 | Lamond | 260/410.6 |
| 4,849,242 | 7/1989 | Kershner | 426/601 |
| 4,861,613 | 8/1989 | White | 426/611 |
| 4,980,191 | 12/1990 | Christensen | 426/601 |
| 4,983,329 | 1/1991 | Cooper | 260/410.7 |
| 5,059,443 | 10/1991 | Ennis | 426/804 |
| 5,077,073 | 12/1991 | Ennis et al. | 426/531 |
| 5,118,448 | 6/1992 | Cooper | 554/168 |
| 5,135,683 | 8/1992 | Cooper | 554/151 |
| 5,137,743 | 8/1992 | Zaks et al. | 426/602 |
| 5,175,323 | 12/1992 | Cooper | 554/164 |
| 5,213,802 | 5/1993 | Masten | 424/439 |
| 5,219,604 | 6/1993 | Klenmann et al. | 426/531 |
| 5,266,346 | 11/1993 | Klemann et al. | 426/611 |
| 5,273,772 | 12/1993 | Cooper | 426/611 |
| 5,308,634 | 5/1994 | Cooper | 426/611 |
| 5,319,048 | 6/1994 | Carosino | 527/300 |

FOREIGN PATENT DOCUMENTS

| | | |
|---|---|---|
| 415636A2 | 3/1991 | European Pat. Off. . |
| 433016A2 | 6/1991 | European Pat. Off. . |
| 481523A1 | 4/1992 | European Pat. Off. . |
| 0481717 | 4/1992 | European Pat. Off. . |
| 1595369 | 4/1970 | Germany . |
| 207070 | 2/1984 | Germany . |
| WO92/01386 | 2/1992 | WIPO . |

OTHER PUBLICATIONS

CA94 (26):214395x.
Mieth; G. et al "Acaloric Compounds With Fat–Like Functional Properties Die Nahrung", vol. 27, No. 9, pp. 853–876, 1983.
Aust. et al. "Orientational Studies on the Meta Bolism of Various Acaloric Compounds with Fat–Like Properties in the Rat", Die Nahrung vol. 32 No. 1, pp. 49-5-7–1988.

Primary Examiner—Carolyn Paden
Attorney, Agent, or Firm—Stephen D. Harper

[57] ABSTRACT

Reduced calorie food compositions are prepared using linked esterified alkoxylated polyol fat substitutes comprised of polyether glycol linking segments, polyol segments, and fatty substituents (which may be fatty acid ester and/or fatty acid-esterified oxyalkylene segments). The fat substitutes are obtainable by alkoxylating a polyol such as glycerin with a monoepoxide such as propylene oxide and a polyepoxide-functionalized polyether glycol (either simultaneously or sequentially) and esterifying the resulting alkoxylated polyol with a fatty acid or its equivalent. Alternatively, the polyepoxide-functionalized polyether glycol could be condensed with a fatty acid partial ester of a polyol or an alkoxylated fatty acid partial ester of a polyol.

25 Claims, 1 Drawing Sheet

LINKED ESTERIFIED ALKOXYLATED POLYOLS USEFUL AS REDUCED CALORIE FAT SUBSTITUTES

FIELD OF THE INVENTION

This invention relates to reduced calorie fat substitutes which are esterified alkoxylated polyols containing polyether glycol linking segments. The linked esterified alkoxylated polyols are useful as fully functional replacements for edible lipids in the preparation of food compositions having significantly decreased caloric content as compared to analogous compositions prepared using natural fats and oils. The fat substitutes contain a reduced number of hydrolyzable ester bonds as compared to analogous substances utilizing ester-bridged side chains.

BACKGROUND OF THE INVENTION

The consumption of high levels of triglyceride lipids has been associated with a number of health problems. Currently, obesity is one of the more prevalent metabolic problems among the general population. This condition in many people is attributed to the ingestion of a greater number of calories than is actually needed to supply energy for the maintenance and functioning of the body. Lipids are the most concentrated form of energy in the diet, with each gram of a triglyceride contributing about nine calories.

Maintaining a strict low fat diet, however, is difficult due to the fact that most persons prefer the taste of "rich" foods, that is, foods that have the satisfying mouthfeel associated with fats and oils. In order for a reduced calorie food composition to satisfactorily replace a conventional foodstuff, the fat substitute used in its preparation must mimic as closely as possible the organoleptic qualities of a triglyceride. The fat substitute must additionally have physical properties (viscosity, melting point, heat stability, thermal conductivity, etc.) resembling those of natural lipids since such properties often play a key role during preparation of a food composition. For example, in deep fat frying the oil acts as a heat transfer medium so as to impart crispiness to the food being fried. At the same time, the ideal fat substitute should be non-toxic and should not cause any undesirable gastrointestinal side effects such as anal oil leakage, gas formation or diarrhea. This combination of attributes has in practice been quite difficult to achieve; the need to develop completely acceptable reduced calorie fat substitutes thus still exists.

U.S. Pat. No. 5,219,604 (Klemann et al.) teaches the use in fat substitutes of inter- and intramolecular ester bridges of the formula —O—(CO)—$(CH_2)_n$—(-CO)—O— where n is 1 to 8 formed by reacting dibasic acids with hydroxyl groups on the fatty side chains of fat compounds. Such fat substitutes, through the incorporation of hydroxy acids, thus inherently contain multiple ester linkages capable of being hydrolyzed upon ingestion. Where such hydrolysis takes place, the resulting hydrozylates are susceptible to further digestion; such fat substitutes may therefore have a higher level of available calories than otherwise would be desirable. Moreover, hydroxy fatty acids have certain deleterious physiological effects. The use of hydroxy fatty acids to prepare a fat substitute thus may not be desirable if digestion of the fat substitute will release such substances in the digestive tract.

SUMMARY OF THE INVENTION

This invention provides a linked esterified alkoxylated polyol useful as a reduced calorie fat substitute comprised of at least one polyether glycol linking segment, at least two polyol segments, wherein each polyol segment is connected to a polyether glycol linking segment either directly or through an unesterified oxyalkylene segment, and at least one fatty substituent selected from fatty acid ester groups and fatty acid-esterified oxyalkylene segments attached to a polyol segment.

In a preferred embodiment, the fat substitute has a molecular weight of from 750 to 6000 and is comprised of:

(a) at least one polyether glycol linking segment having the general structure

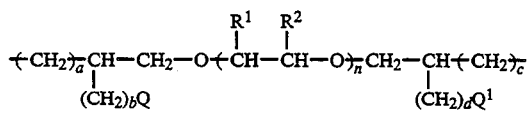

wherein n is an integer of from 1 to 20, Q and $Q^1$ are the same or different and are independently selected from hydroxy groups, fatty acid ester groups, hydroxy-terminated oxyalkylene segments, and fatty acid-esterified oxyalkylene segments, a and b are different and are 0 or 1, c and d are different and are 0 or 1 and $R^1$ and $R^2$ are the same or different and are selected from hydrogen and $C_1$-$C_6$ alkyl;

(b) from two to four polyol segments derived from an aliphatic polyol having from 3 to 8 hydroxyl groups, wherein each polyol segment is connected to a polyether glycol linking segment, either directly or through an unesterified oxyalkylene segment having the general structure

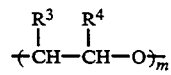

wherein m is an integer of from 1 to 20 and $R^3$ and $R^4$ are the same or different and are independently selected from hydrogen and $C_1$-$C_6$ alkyl; and (c) at least one fatty acid-esterified oxyalkylene segment attached to a polyol segment having the general structure

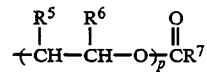

wherein $R^5$ and $R^6$ are the same or different and are independently selected from hydrogen and $C_1$-$C_6$ alkyl, $R^7$ is a $C_5$-$C_{23}$ hydrocarbyl group, and p is an integer of from 1 to 20, wherein the number of polyether glycol linking segments is one less than the number of polyol segments and the number of fatty acid-esterified oxyalkylene segments is at least equal to the number of polyol segments.

The linked esterified alkoxylated polyols of this invention are obtainable, for example, by reaction of a polyepoxide-functionalized polyether glycol, a $C_2$-$C_6$ aliphatic mono-epoxide, a polyol, and a fatty acid entity such as a free fatty acid, fatty acid halide, fatty acid ester, or fatty acid anhydride.

Also provided by this invention is a fat component useful for preparing a reduced calorie food product, said fat component comprising an edible triglyceride and the linked esterified alkoxylated polyol. The invention also furnishes a reduced calorie food product comprised of a fat component, said fat component comprising the aforedescribed linked esterified alkoxylated polyol fat mimetic.

DETAILED DESCRIPTION OF THE INVENTION

Figure 1:
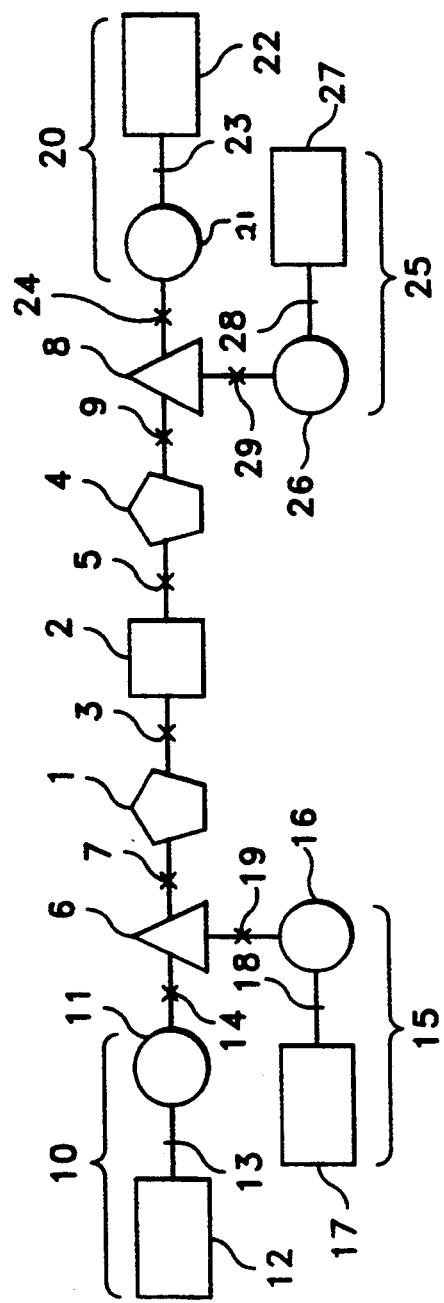
FIG. 1 illustrates in schematic form an exemplary linked esterified alkoxylated polyol of this invention.

The linked esterified alkoxylated polyol fat substitutes of this invention are organic compounds comprised of at least three types of covalently bonded moieties; namely, (1) polyether glycol linking segments, (2) polyol segments, and (3) fatty substituents (which may take the form of fatty acid ester groups and/or fatty acid-esterified oxyalkylene segments). These moieties are connected to each other through ether or ester bonds. In a preferred embodiment, the total number of glycol linking segments, unesterified oxyalkylene segments, and fatty substituents attached to each polyol segment is equal to the number of hydroxyl groups on the polyol from which said polyol segment is derived. However, it is also possible for a portion of the hydroxyl groups on the polyol to remain as free (unreacted) hydroxyl groups pendant to the polyol segment in the linked esterified alkoxylated polyol. Preferably, no more than one hydroxyl group is pendant to each polyol segment.

The polyether glycol linking segments function so as to link together polyol segments within the fat substitute either directly or through intervening unesterified oxyalkylene segments and are characterized by the presence of one or more repeating units each containing from 2–4 carbon atoms and one oxygen atom in its backbone together with a pendant group (i.e., a group other than hydrogen) on the alpha or beta carbon at each terminus of the polyether glycol linking segment selected from hydroxy groups, hydroxy-terminated oxyalkylene segments, fatty acid ester groups, and fatty acid-esterified oxyalkylene segments. The position of each pendant group will be determined by the direction of epoxide-ring opening which takes place during synthesis of the linked esterified alkoxylated polyol, as will be explained in detail subsequently. The polyether glycol linking segments may be linear or branched in structure. While the identity of the remainder of the polyether glycol linking segment is not critical, it is generally preferred that it be aliphatic in character and not contain any aromatic, nitrogenous, or halogenated groups. Carbon-carbon double bonds or alicyclic groups may advantageously be present, however. In the embodiment of this invention wherein the polyether glycol linking segment is difunctional, the number of polyether glycol linking segments per molecule is preferably one less than the number of polyol segments.

In one desirable embodiment, the polyether glycol linking segment corresponds to the general structure

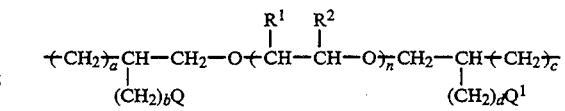

wherein n is an integer of from 1 to 40 (more preferably, 1 to 20), Q and $Q^1$ are the same or different and are independently selected from hydroxy groups (i.e., Q or $Q'=OH$), fatty acid ester groups, hydroxy-terminated oxyalkylene segments, and fatty acid-esterified oxyalkylene segments, a and b are different and are 0 or 1, c and d are different and are 0 or 1, and $R^1$ and $R^2$ are the same or different and are selected from hydrogen and $C_1$–$C_6$ alkyl. In one embodiment, where a and c are equal to 1 and b and d are equal to 0 (as will result when the linked esterified alkoxylated polyol is prepared by reacting an alkoxylated polyol with a diglycidyl reactant and the hydroxyl group of the alkoxylated polyol adds to the less substituted carbon atom (i.e., —CH$_2$— rather than

of the epoxide ring of the diglycidyl reactant), the structure of the polyether glycol linking segment is as follows:

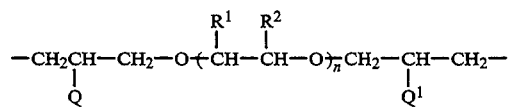

Suitable fatty acid ester groups (for use as Q and/or Q') include those derived from linear, branched, saturated, or unsaturated $C_6$–$C_{24}$ fatty acids such as those obtainable from hydrolysis (splitting) of triglycerides. Illustrative hydroxy-terminated oxyalkylene segments include those segments having the general structure

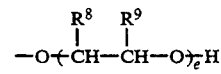

wherein $R^8$ or $R^9$ are the same or different and are independently selected from hydrogen and $C_1$–$C_6$ alkyl and e is an integer of from 1 to 40 (more preferably, 1 to 20). Preferably, at least one of $R^8$ or $R^9$ is hydrogen with the other R group being hydrogen, methyl or ethyl. Examples of fatty acid-esterified oxyalkylene segments include those corresponding to the general structure

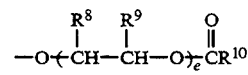

where $R^8$, $R^9$ and e have the same meaning as described hereinabove for illustrative hydroxy-terminated oxyalkylene segments and $R^{10}$ is a $C_5$–$C_{23}$ hydrocarbyl group (including branched, linear, saturated, or unsaturated groups). The acyl group

is preferably derived from a fatty acid or equivalent thereof.

The polyether glycol linking segments in the linked esterified alkoxylated polyols of this invention may be suitably derived from polyepoxide-functionalized polyether glycols. Such substances are characterized by having two or more epoxide (oxirane) functional groups present therein capable of undergoing ring-opening reactions to form ether bonds. In a desirable embodiment, the polyepoxide-functionalized polyether glycol is a diglycidyl reactant having the general structure

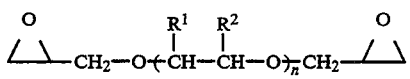

wherein n is an integer of from 1 to 40 (more preferably, 1 to 20) and $R^1$ and $R^2$ are the same or different and are selected from hydrogen and $C_1$–$C_6$ alkyl (especially methyl and ethyl). The epoxide groups may bear additional substituents such as, for example, methyl or ethyl groups at any of the three carbons of the glycidyl functionality. Such diglycidyl reactants are well-known in the art and may be readily prepared, for example, by reacting epichlorohydrin with a polyether glycol obtainable by ring-opening polymerization of an epoxide such as polyethylene glycol, polypropylene glycol, polybutylene glycol, or a mixed polyoxyalkylene glycol such as a hydroxy-terminated ethylene oxide/propylene oxide or propylene oxide/1,2-butene oxide copolymer. Analogous polyglycidyl reactants containing more than 2 epoxide groups may be similarly obtained by derivatizing branched polyether glycols containing three, four, five, six, seven, eight or more hydroxyl groups with epichlorohydrin. The polyether polyol starting materials in the foregoing embodiments may be derived by ring-opening polymerization of an epoxide such as ethylene oxide, propylene oxide, 1,2-butene oxide or the like onto a polyhydric initiator such as a diol (e.g., 1,4-butanediol, dipropylene glycol, ethylene glycol), a triol (e.g., glycerin, trimethylolpropane), a sugar alcohol, a monosaccharide, a disaccharide, pentaerythritol (or another aliphatic tetrol) or the like. Polyepoxide-functionalized polyether glycols in a preferred embodiment correspond to the general structure

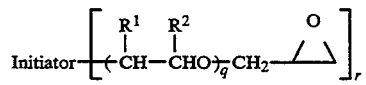

wherein Initiator is the organic residue derived from the polyhydric initiator, $R^1$ and $R^2$ are the same or different and are selected from hydrogen and $C_1$–$C_6$ alkyl (preferably, methyl or ethyl), q is zero or an integer of from 1 to 40 (preferably, 1 to 20), and r is preferably an integer of from 2 to 8. Suitable polyepoxide-functionalized polyether glycols also include those substances obtainable by functionalization of a polytrimethylene glycol (i.e., a polymerized oxetane), polytetramethylene glycol (i.e., a polymerized oxolane such as tetrahydrofuran) or glycerol oligomer with two or more epoxide groups. Where n=1 or q=0 in the structures shown hereinabove, the starting material for the polyepoxide-functionalized polyether glycol may be a monomeric species such as propylene glycol, ethylene glycol, 1,4-butanediol, 2,3-butanediol, 1,3-propanediol, neopentyl glycol, trimethyl propane, glycerol, 1,2,6-hexanetriol, 1,6-hexanediol, sorbitan, pentaerythritol, a sugar alcohol, or the like.

Methods of preparing suitable polyepoxide-functionalized polyether glycols are well-known in the art and are described, for example, in U.S. Pat. No. 4,287,078 (Langdon et al.), Japanese Kokai No. 01-151,567 (Chem. Abst. 112:214404f), Japanese Kokai No. 82-31,921 (Chem. Abst. 97:24655w), Japanese Kokai No. 63-115,877 (Chem. Abst. 109:23084u), U.S. Pat. No. 3,240,376 (Smith et al.), and U.S. Pat. No. 2,854,461 (De Groote et al.), the teachings of which are incorporated herein by reference in their entirety. Certain polyepoxide-functionalized polyether glycols are also available commercially; for example, Aldrich Chemical Company sells poly (propylene glycol) diglycidyl ether having a molecular weight of about 640.

The linked esterified alkoxylated polyols of this invention contain a minimum of two polyol segments, but may also contain three, four, or an even higher number of such segments depending upon the extent of branching and cross linking. To limit viscosity, it will generally be desirable for the linked esterified alkoxylated polyol to contain no more than four polyol segments. Each polyol segment will correspond to the generic formula R—(O)—$_n$ and is derived from a polyol or a polyol equivalent wherein the polyol is a polyhydric alcohol containing three or more hydroxyl groups. R in the foregoing formula thus is an organic moiety such as a hydrocarbyl group containing at least three carbon atoms, hydrogen, and, optionally, other elements such as oxygen or nitrogen. The number of hydroxyl groups on the polyol (n) is most suitably from 3 to 8. The polyol (which preferably contains primary and/or secondary hydroxyl groups) may be selected from $C_3$–$C_{12}$ aliphatic triols (e.g., glycerol, 1,2,4-butanetriol, 2,3,4-pentanetriol, 2-ethyl-2-(hydroxymethyl)-1,3-propanetriol (trimethylol propane), 1,1,1-tris(hydroxymethyl)ethane, 1,2,6-trihydroxyhexane, 1,2,3-heptanetriol, and the like), $C_4$–$C_{12}$ aliphatic tetrols (e.g., 2, 3, 4, 5-hexanetetrol, sorbitan, erythritol, pentaerythritol), $C_5$–$C_8$ sugar alcohols [including those compounds corresponding to the formula $HOCH_2(CHOH)_nCH_2OH$ wherein n is 3 to 6 such as xylitol, sorbitol, arabitol, mannitol, and the like], monosaccharides (e.g., erythrose, threose, ribose, arabinose, xylose, lyxose, allose, altrose, glucose, mannose, gulose, idose, galactose, fructose, galactose, and the like), disaccharides (e.g., sucrose, lactose, maltose) and alkyl glycosides (e.g., methyl glycosides, ethyl glycosides, propyl glycosides, and other glycoside molecules wherein the alkyl glycoside is an acetal formed by interaction of a $C_1$–$C_{20}$ alcohol with a carbonyl group of a mono- or disaccharide such as glucose). Also suitable for use as the polyol are hydroxy-containing substances such as tetrahydrofuran oligomers, oxetane oligomers, sorbitol oligomers, glycerol oligomers, and the like.

In a preferred embodiment, the polyol is glycerin so as to provide polyol segments having the structure

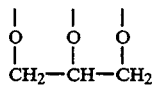

in the linked esterified alkoxylated polyol (i.e., R=C$_3$H$_5$ and n=3 in the foregoing formula). Glycerin may be readily and economically obtained by hydrolyric splitting of a natural triglyceride. The fatty acids obtained in such a splitting operation may also be utilized in the preparation of the linked esterified alkoxylated polyol.

Each polyol segment is connected to at least one polyether glycol linking segment either directly or through an unesterified oxyalkylene segment. In each case, ether bonds rather than ester bonds are present between polyol segments and polyether glycol linking segments. The unesterified oxyalkylene segments are preferably each comprised of an ether oxygen and one or more poly-carbon-oxygen sequences, i.e.,

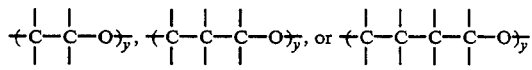

wherein y is at least 1 and preferably is not more than 20 (more preferably, not more than 10). An individual oxyalkylene segment may thus be monomeric or oligomeric in character and may be derived by ring-opening of a cyclic ether such an oxetane, oxolane, or epoxide. Especially preferred for use are C$_2$–C$_{10}$ aliphatic monoepoxides such as, for example, ethylene oxide, propylene oxide, 1,2-butene oxide, 2,3-butene oxide (cis and/or trans), isobutylene oxide, 1,2-pentene oxide, 2,3-pentene oxide, cyclopentene oxide, 1,2-hexene oxide, cyclohexene oxide, and the like and mixtures thereof. In certain embodiments of this invention, the use of un- or mono-substituted 1,2-alkylene oxides such as ethylene oxide, propylene oxide and 1,2-butene oxide is particularly desirable. An oxyalkylene segment thus may preferably have the general structure

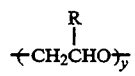

wherein R is hydrogen or C$_1$–C$_6$ alkyl (methyl, ethyl, cyclohexyl, and the like) and y is an integer of from 1 to 10. The value of y may, of course, vary between individual unesterified oxyalkylene segments within the same linked esterified alkoxylated polyol. An oxyalkylene segment may advantageously be comprised of different types of ring-opened epoxide units (for example, both oxyethylene and oxypropylene units) which are present in either a random or block configuration.

The fatty substituents are attached to the polyol segments through ester or ether bonds and may be either fatty acid ester groups or fatty acid-esterified oxyalkylene segments (both types of fatty substituents may be present in the same molecule of linked esterified alkoxylated polyol if so desired). In a preferred embodiment, the number of fatty substituents is at least equal to the number of polyol segments.

The fatty acid ester groups, if present, are attached directly to the polyol segments through ester bonds. Such groups preferably correspond to the general structure

wherein R is a C$_5$–C$_{23}$ hydrocarbyl group (linear or branched, saturated, monounsaturated, or polyunsaturated). The fatty acid ester groups are desirably derived from monocarboxylic fatty acids or their equivalents (halide, ester, anhydride). Such fatty acids and their equivalents (hereinafter referred to at times collectively as "fatty acid entities") are readily available at low cost from natural sources such as edible triglycerides. Specific illustrative fatty acids suitable for use include, but are not limited to, eicosanoic (arachidic) acid, heneicosanoic acid, docosanoic (behenic) acid, tricosanoic acid, tetracosanoic (lignoceric) acid, caprylic acid, pelargonic acid, capric acid, caproic acid, lauric acid, palmitic acid, stearic acid, eleic acid, cetoleic acid, myristic acid, palmitoleic acid, gadoleic acid, erucic acid, ricinoleic acid, linoleic acid, linolenic acid, myristoleic acid, eleostearic acid, elaidic acid, arachidonic acid, or mixtures of these acids. The fatty acids may be derived synthetically or from natural sources such as triglyceride lipids. Mixtures of fatty acid entities, such as the mixtures of fatty acids typically obtained by hydrolysis (splitting) of a triglyceride such as corn oil or soybean oil, may advantageously be used. Other illustrative preferred fatty acid entities include the acid chlorides and methyl or ethyl esters of the aforementioned fatty acids.

The relative proportions of fatty acid-esterified oxyalkylene segments and fatty acid ester groups functioning as fatty substituents in the linked esterified alkoxylated polyol are not critical and may be varied as desired to achieve favorable properties in the fat substitute. Either type of fatty substituent may be utilized exclusively; alternatively, both types may be present simultaneously within the same molecule.

The fatty acid-esterified oxyalkylene segments are individually comprised of both an oxyalkylene segment and a fatty acid acyl group. Said oxyalkylene segment may correspond in structure to the unesterified oxyalkylene segments described previously hereinabove (e.g., oxyethylene, polyoxyethylene, oxypropylene, polyoxypropylene, oxybutylene, polyoxybutylene). The fatty acid acyl group, which is connected to the oxyalkylene segment of the fatty acid-esterified oxyalkylene segment by an ester bond, preferably has the general structure

wherein R is a C$_5$–C$_{23}$ hydrocarbyl group (linear or branched; saturated, monounsaturated, or polyunsaturated). The fatty acid acyl group is desirably derived from a monocarboxylic fatty acid or equivalent (halide, ester, anhydride) including the fatty acids discussed and described hereinabove in connection with the fatty acid ester groups.

The properties and characteristics of the linked esterified alkoxylated polyol may be varied or controlled as desired by adjusting the relative proportions of fatty substituents to polyether glycol linking segments. Decreasing the fatty substituent: polyether glycol linking segment ratio generally will increase the molecular weight of the linked esterified alkoxylated polyol, for example. The precise ratio selected for use is not critical and may vary within wide limits depending upon other factors such as, for example, the number of hydroxyl groups on the polyol and the number of epoxide functionalities on the polyepoxide-functionalized polyether glycol. Where the polyol has three hydroxyl groups and the polyepoxide-functionalized glycol is a diglycidyl-functionalized polypropylene glycol, for example, illustrative ratios which are suitable for use include 4: 1, 5:2, 6:3, and 7:4.

In preferred embodiments of the invention, the structures of the various ester bonds incorporated in the linked esterified alkoxylated polyol are controlled such that differential reactivity with respect to hydrolytic cleavage by digestive enzymes such as lipase is attained. This results not only in a reduction in effective caloric value as compared to a triglyceride, but also the selective conversion of the fat substitute to a product or intermediate which is less oil-like in nature. The product of such a controlled digestive process (i.e., following hydrolysis) may have decreased hydrophobicity, and thus greater hydrophilicity, relative to the parent linked esterified alkoxylated polyol. The product thus produced may also have a higher solid fat index or a higher melting point at body temperature than the original fat substitute. Such a product of a process of controlled digestion will tend to have not only decreased oiliness, but may also function as a emulsifier or surface active agent capable of emulsifying any undigested fat substitute or oil-like digestive by-products. Thus, the fat substitutes of this invention can be selected such that they will have the taste and appearance of triglycerides, yet will be less prone to exit the gastrointestinal tract as a persistent oil compared to certain substances taught as fat substitutes in the prior art.

One method by which the relative digestibility of the linked esterified alkoxylated polyol may be adjusted as may be desired for a particular application is to vary the extent of stearic hindrance present at the ester linkages. For example, bulky substituents may be introduced on the carbon atoms adjacent to the ester oxygen atom or the ester carbonyl group carbon atom so as to block or interfere with the ability of the ester bond to closely associate with the active sites on the lipase enzymes responsible for catalyzing ester hydrolysis. Where the fatty substituent is a fatty acid ester group attached directly to one of the primary (end) carbon atoms of glycerin (which serves as a polyol segment), for instance, the ester bond formed will generally be more susceptible to enzymatic cleavage when ingested than if the fatty substituent is a fatty acid-esterified oxypropylene segment wherein a methyl group is present on the carbon atom adjacent to the ester oxygen. Another approach is to use a polyol such as sucrose having a large number (e.g., 6 or more) of closely spaced (e.g., separated by no more than 3 carbon atoms) hydroxy groups to form the polyol segments. The relatively large number of fatty substituents attached to the polyol segment will tend to render the individual ester bonds much less accessible to lipase enzyme and thus reduce the degree to which the linked esterified alkoxylated polyol is metabolized by the human body.

To better illustrate the interrelationships between the different components of the linked esterified alkoxylated polyol fat substitute of this invention, an example of such a substance is diagrammed schematically in FIG. 1. In this illustrative example, unesterified oxyalkylene segment 1 is attached to polyether glycol linking segment 2 by ether bond 3. Unesterified oxyalkylene segment 4 is also attached to 2 by ether bond 5. Polyol segment 6 is attached to 1 through ether bond 7, while polyol segment 8 is similarly attached to 4 through ether bond 9. Fatty acid-esterified oxyalkylene segment 10, comprised of oxyalkylene segment 11 and fatty acid acyl group 12 joined by ester bond 13, is attached to 6 through ether bond 14. Fatty acid-esterified oxyalkylene segment 15, comprised of oxyalkylene segment 16 and fatty acid acyl group 17 joined by ester bond 18, is attached to 6 through ether bond 19. Fatty acid-esterified oxyalkylene segment 20, comprised of oxyalkylene segment 21 and fatty acid acyl group 22 joined by ester bond 23, is attached to 8 by ester bond 24. Fatty acid esterified oxyalkylene segment 25, comprised of oxyalkylene segment 26 and fatty acid acyl group 27 joined by ester bond 28, is attached to 8 through ether bond 29. Variations upon this structure will be readily apparent to the person of ordinary skill in the art familiar with the teachings of the instant specification. For example, fatty acid-esterified oxyalkylene segment 10 could be replaced by another unesterified oxyalkylene segment and polyether glycol linking segment, the latter being connected to additional polyol and/or fatty acid-esterified oxyalkylene segments. In another variation, one or both of unesterified oxyalkylene segments 1 and 4 could be omitted, resulting in direct attachment of polyether glycol linking segment 2 to polyol segments 6 and 8. Alternatively, one or more of fatty acid-esterified oxyalkylene segments 10, 15, 20, or 25 could be replaced by a fatty acid ester group such as stearyl or oleoyl.

The structure of a specific example of a linked esterified alkoxylated polyol within the class of fat substitutes embraced by the present invention may be represented as follows (wherein $C_3H_6O$ is oxypropylene):

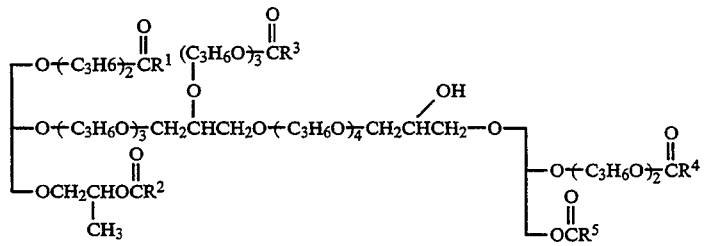

To minimize direct absorption of the fat substitute through the walls of the gastrointestinal tract, it is highly advantageous for the molecular weight of the linked esterified alkoxylated polyol to be at least 750 (more preferably, at least 900). To avoid undesirably high viscosities, the molecular weight generally should be no greater than 6000 and preferably is 3000 or less. It will be particularly advantageous (where the linked esterified alkoxylated polyol is to be used to replace most or all of the triglyceride portion of a food composition) to control the molecular weight, degree of cross-linking, and other structural parameters such that the viscosity of the linked esterified alkoxylated polyol is less than 1000 cps (more preferably, less than 500 cps; most preferably, less than 280 cps) as measured by Brookfield viscometer at 100° F. (38° C.).

The higher molecular weight linked esterified alkoxylated polyol, while perhaps too viscous to be easily used alone as 100% replacements for triglycerides in the fat component of a food composition may be advantageously blended with low viscosity digestible triglycerides or non-linked esterified alkoxylated polyol (or other fat substitute such as sucrose polyester). Such linked esterified alkoxylated polyols may beneficially act as gelling or thickening agents. For example, when combined at the 0.5 to 25 weight % level with liquid unsaturated triglycerides, higher molecular weight linked esterified alkoxylated polyols in accordance with this invention may modify the viscosities or melting properties of such triglycerides such that they closely resemble those of solid or semi-solid fats containing high levels of saturated fatty acids. Alternatively, the tendency of a liquid fat substitute such as certain liquid non-linked esterified alkoxylated polyols to exhibit anal oil leakage when consumed in large quantities may be effectively suppressed by incorporation of the linked esterified alkoxylated polyol. Reduced calorie fat substitutes comprised of liquid triglyceride, liquid non-linked esterified alkoxylated polyols, and higher molecular Weight linked esterified alkoxylated polyols may also provide certain advantages (e.g., reduced oil leakage as compared to analogous compositions not containing the linked esterified alkoxylated polyol).

In a preferred embodiment of this invention, the total number of equivalents of ring-opened monoepoxide per linked esterified alkoxylated polyol molecule is at least 4 but no greater than 40. As is evident from the description hereinabove, the ring-opened monoepoxide may be variously present in the polyglycol ether linking segments, the unesterified oxyalkylene segments, and/or in the fatty acid-esterified oxyalkylene segments.

The linked esterified alkoxylated polyol fat substitutes will deliver less than 9 Kcal/gram, preferably less than 5 Kcal/gram, and, in some embodiments, less than 3 Kcal/gram, upon being metabolized by the human body. Where a maximum reduction in the caloric content of a food composition is desired, the linked esterified alkoxylated polyol may be selected such that it delivers essentially 0 Kcal/gram when consumed.

The linked esterified alkoxylated polyols of this invention may be prepared by adaptation of conventional alkoxylation and esterification techniques. For example, the fat substitutes may be obtained as the reaction product of a polyepoxide-functionalized polyether glycol, a $C_2$–$C_6$ aliphatic monoepoxide, a polyol, and a fatty acid entity (e.g., free fatty acid, fatty acid halides, fatty acid esters, fatty acid anhydrides). These reactants may be combined in a number of different ways so as to yield the desired linked esterified alkoxylated polyol. The precise method utilized is not critical, but certain properties and characteristics of the product may be favorably influenced by the manner in which said reactants are deployed. Some of the different procedures which may be utilized are as follows:

(a) A polyol such as glycerin may be reacted with the desired number of equivalents of a monoepoxide in the presence of an appropriate catalyst such as a base or acid so as to ring-open the epoxide and to add the epoxide onto the hydroxyl groups of the polyol to form an alkoxylated polyol. The alkoxylated polyol may then be reacted with a suitable polyepoxide-functionalized polyether glycol in the presence of an appropriate catalyst (for example, a basic catalyst such as alkali metal or an acidic catalyst such as $BF_3$ etherate). The hydroxy groups on the alkoxylated polyol will react at the epoxide groups of the polyepoxide-functionalized polyether glycol to generate new hydroxy groups through ring-opening of the polyepoxide-functionalized polyether glycol. The polyether glycol-linked intermediate thus formed may then be directly esterified with the fatty acid entity so as to place fatty acid acyl groups on the molecule. Alternatively, the polyether glycol-linked intermediate may be further reacted with additional monoepoxide prior to esterification.

(b) The polyol may also be reacted simultaneously with both the monoepoxide and the polyepoxide-functionalized polyether glycol to obtain a polyether glycol-linked intermediate. The intermediate may then be esterified with the fatty acid entity.

(c) The polyepoxide-functionalized polyether glycol could alternatively be first reacted with the polyol, followed by alkoxylation with the monoepoxide. Esterification with a fatty acid or equivalent would lead to the desired linked esterified alkoxylated polyol fat substitute.

(d) In yet another synthetic variation, the polyol could be first reacted with the monoepoxide and then partially esterified with a fatty acid entity so as to incompletely convert the hydroxyl groups of the alkoxylated polyol to long chain fatty acid ester groups. The remaining hydroxyl groups could then be reacted with the polyepoxide-functionalized polyether glycol to form a linked esterified alkoxylated polyol wherein the polyether glycol linking segments bear hydroxy groups. These hydroxy groups may be esterified directly with a fatty acid entity (to yield fatty acid ester substituent), alkoxylated with an appropriate monoepoxide, or alkoxylated and then esterified with a fatty acid entity.

(e) Another approach is to simultaneously react monoepoxide, polyol, and triglyceride in the presence of base or other suitable catalyst to form a partially esterified alkoxylated polyol and to thereafter react with the desired amount of polyepoxide-functionalized polyether glycol so as to generate polyether glycol linking segments. Alternatively, all four reactants could be simultaneously reacted followed by, if desired, esterification of any unreacted hydroxyl groups with a fatty acid entity or further alkoxylation and then esterification.

It may be advantageous to utilize reactants such as fatty acid partial esters of polyols, alkoxylated fatty acid partial esters of polyols, and the like. Reactants of this type are well-known and are available from commercial sources or may be synthesized using standard methods. For example, polyols such as glycerin, sugars, sugar alcohols, and the like may be partially esterified with fatty acids so as to provide fatty acid partial esters of said polyols containing unreacted hydroxyl groups as well as fatty acid ester groups. Such substances may be further reacted with aliphatic epoxides such as ethylene oxide and propylene oxide to furnish alkoxylated fatty acid partial esters of the polyols. As is well known in the field, alkoxylated fatty acid partial esters of polyols may also be prepared by direct simultaneous reaction of epoxides, triglycerides, and polyols. Specific illustrative examples of suitable reactants of this type include polyglyceryl partial esters of fatty acids, ethoxylated and/or propoxylated polyglyceryl partial esters of fatty acids, mono- and di-glycerides (e.g., glycerol dilaurate, glycerol dibehenate, glycerol mono-stearate, glycerol mono-oleate), ethoxylated, propoxylated, and/or butoxylated mono- and di-glycerides, sorbitan partial esters (e.g., sorbitan tristearate or trioleate), and the like. The aforedescribed fatty acid partial esters of polyols and alkoxylated fatty acid partial esters of polyols may be condensed or reacted with the polyepoxide-functionalized polyether glycol in the presence of an appropriate catalyst, followed by (if so desired) alkoxylation with a mono-epoxide and/or esterification with a fatty acid entity, to generate the linked esterified alkoxylated polyol fat substitute.

One means of introducing fatty acid ester groups attached directly to polyol segments is to block one or more of the polyol hydroxyl groups with a protective group such as ketal, acetal, benzyl, tertiary alkyl, tetrahydropyranyl, or triphenyl methyl which is stable to the alkoxylation conditions utilized, subject the blocked polyol to alkoxylation, then remove the protective group(s) prior to or concurrent with esterification using a suitable method such as acidic hydrolysis or hydrogenation.

The fatty acid entity employed in the aforedescribed esterification steps may preferably be a fatty acid or fatty acid ester having the general structure wherein R is a $C_5$–$C_{23}$ olefinic (monounsaturated or polyunsaturated) or paraffinic (saturated) hydrocarbon radical and R is hydrogen or a $C_1$–$C_6$ hydrocarbon radical. Examples of suitable fatty acids include, but are not limited to, caprylic, capric, lauric, myristic, myristoleic, stearic, isostearic, palmitic, palmitoleic, rincinoleic, linoleic, elaidic, linolenic, elaeostearic, arachidic, arachidonic, behenic, erucic, oleic, and heptadecanoic acid. Short chain, medium chain, and long chain fatty acids, as well as any and all combinations thereof are all suitable for use. The fatty acids may be derived synthetically or from natural sources such as triglyceride lipids. Exemplary fatty acid esters include the methyl, ethyl, propyl, and isopropyl esters of the foregoing fatty acids. Mixtures of fatty acid entities, such as the mixtures of fatty acids typically obtained by hydrolysis (splitting) of a triglyceride such as corn oil or soybean oil, may be used to advantage.

Fatty acid halides which may be used can have the general structure

wherein R is a $C_5$–$C_{23}$ olefinic or paraffinic hydrocarbon radical and X is halide, preferably chloride or bromide. Fatty acid anhydrides suitable for use may correspond to the general formula

wherein R and $R^1$ are the same or different and are independently selected from $C_5$–$C_{23}$ olefinic (monounsaturated, polyunsaturated) or paraffinic hydrocarbon radicals.

The alkoxylated polyol intermediate (or the alkoxylated polyol) and the fatty acid entity are reacted for a time and at a temperature sufficient to accomplish the desired degree of esterification of the hydroxyl groups of the other reactant. The optimum reaction conditions will vary somewhat depending upon the particular type of fatty acid entity used. If a fatty acid or fatty acid ester is utilized, the reaction temperature is preferably from about 100° C. to 350° C.; reaction times of from about 0.5 to 48 hours are generally sufficient to accomplish substantially complete esterification of the hydroxyl groups. A co-product having the structure HOR' (i.e., water or an alcohol) will be generated as esterification proceeds. To drive the reaction to completion, it is desirable to remove the co-product from the reaction mixture as it forms by a suitable method such as distillation, sparging, or vacuum stripping. A catalyst may be employed if desired to shorten the reaction time required. If the fatty acid entity is a free fatty acid, the catalyst is preferably an acidic catalyst. Suitable acidic esterification catalysts include sulphonic acids, sulfuric acid, phosphorus pentoxide, hypophosphonic acid, cationic exchange resins, tin chloride, titanium alkoxide, aluminum or nickel alloys, zinc chloride or the like. If a fatty acid ester is used, an acidic or basic catalyst may be present during esterification. In a desirable embodiment of the invention which minimizes the number of processing steps required, the same catalyst is used to catalyze the desired alkoxylation, esterification, and/or polyepoxide-functionalized polyether glycol condensation reactions. In this embodiment, the number of intermediate purification steps to remove or neutralize the catalyst is minimized. When the fatty acid compound is a fatty acid halide, somewhat lower reaction temperatures (e.g., about 25° C. to 125° C.) are sufficient, particularly if a tertiary amine such as triethylamine is additionally present to take up the hydrogen halide generated during the esterification reaction. Reaction times of from about 1 to 48 hours are typically sufficient. Similar reaction conditions may be utilized when the fatty acid entity is a fatty acid anhydride such as lauric anhydride or oleic anhydride.

To accomplish (if desired) substantially complete esterification of the intermediate, at least about 1 (more preferably, at least about 1.1) equivalent of the fatty acid entity per equivalent of hydroxyl groups in the alkoxylated polyol or linked alkoxylated polyol is used. For reasons of economy, it is preferred to utilize not more than about 3 equivalents of fatty acid entity per equivalent of hydroxyl groups.

Where the fatty acid entity is a fatty acid and no added acidic catalyst is present, the esterification preferably is self-catalyzed using a slight to moderate excess of fatty acid. In this embodiment, the number of moles of fatty acid is preferably from $1.05 \times n \times$ moles of polyol to $1.40 \times n \times$ moles of polyol (wherein n is an integer of from 3 to 8 and is equal to the number of hydroxyl groups on the polyol).

The fatty acid is preferably a $C_6$–$C_{24}$ saturated or unsaturated (including polyunsaturated and cis or trans) fatty acid and may be either linear or branched in structure. Such substances may be readily obtained from natural sources by the well-known hydrolytic splitting (hydrolysis) of the triglycerides from edible fats and oils. The fat or oil may be fully or partially hydrogenated prior to splitting. Alternatively, the fatty acids may be hydrogenated after hydrolysis or after incorporation into the linked esterified alkoxylated polyol. A single fatty acid or a mixture of different fatty acids may be used.

The relative molar proportions of fatty acid entity and polyepoxide-functionalized polyether polyol utilized may be varied within wide limits to attain the desired ratio of fatty substituents to polyether glycol linking segments in the linked esterified alkoxylated polyol. For example, it will typically be desirable for the amount of fatty acid entity reacted to be from 1 to $n + \frac{1}{2}r - 1$ moles per mole of polyol and the amount of polyepoxide functionalized polyether glycol to be from $1/r$ to $n - 1/r$ moles per mole of polyol where n is equal to the number of hydroxyl groups on the polyol and r is equal to the number of epoxide functionalities in the polyepoxide functionalized polyether glycol (preferably, 2 to 8). In a particularly advantageous embodiment, substantially all (e.g., over 90%) of the available hydroxyl groups are esterified. Incompletely esterified substances will also be suitable for use, however, provided they exhibit physical and organoleptic properties resembling natural fats and oils.

In the embodiment of this invention wherein the polyol is a triol such as glycerin, the polyepoxide functionalized polyether glycol is a diepoxide functionalized polyether glycol, and an average of from 2 to 4 polyol segments per molecule of the linked esterified alkoxylated polyol is desired, the amount of the diepoxide functionalized polyether glycol reacted per mole of polyol should be from 0.5 to 0.75 moles and the amount of fatty acid entity reacted per mole of polyol should be from 1.5 to 3 moles.

Once the desired degree of esterification has been accomplished, any residual unreacted fatty acid entity should be removed from the linked esterified alkoxylated polyol so as to render the fat substitute acceptable for use in food applications. Suitable methods include vacuum steam stripping (distillation) at an elevated temperature (as described, for example, in U.S. Pat. No. 4,983,329), alkali neutralization to precipitate fatty acid salts which may then be removed by filtration, extraction (with methanol, for example), and dilution with a solvent such as hexane in which the desired product is soluble and the fatty acid is insoluble followed by filtration. Unreacted or excess fatty acid ester, fatty acid anhydride, or fatty acid halide may also be removed from the linked esterified alkoxylated polyol by any suitable method. Any catalyst residues present may be neutralized or removed through the use of well-known purification techniques such as extraction, absorption, ion-exchange, or filtration.

The reduced calorie fat substitute can be additionally purified or treated so as to render it more suitable for use in food compositions using any of the techniques known in the art for refining natural vegetable or animal lipids. Such techniques include, but are not limited to, degumming, bleaching, filtration, decolorization, deodorization, hydrogenation, dewaxing, and the like. Various additives such as stabilizers, anti-oxidants (e.g., tocopherols, hindered phenols such as BHT, hydroquinones such as TBHQ), vitamins (e.g., fat-soluble vitamins such as vitamin A, D, E, and K) and so forth can also be incorporated into the linked esterified alkoxylated polyol. Non-linked esterified alkoxylated polyols of the type described in U.S. Pat. Nos. 4,861,613, 5,059,443, 5,077,073 and 4,980,191 and European Pat. Publication No. 481,523 (incorporated herein by reference in their entirety) may also be deliberately blended in any proportion (e.g., 1:99 to 99:1) with the linked esterified alkoxylated polyols of this invention to provide useful reduced calorie fat substitutes.

It should be understood that by the nature of the reactions used in the preparation of the linked esterified alkoxylated polyols as described herein above, the compositions obtained will generally be mixtures of individual compounds which have a range of molecular weight and which may contain structural isomers. Also, depending upon the synthetic procedure used, minor amounts of other materials such as non-linked esterified alkoxylated polyols may be generated together with the linked esterified alkoxylated polyols of this invention. The use of such mixed reaction products as fat substitutes may be advantageous under certain circumstances. For example, the presence of non-linked esterified alkoxylated polyols may beneficially lower the viscosity, hardness, or melting point of a linked esterified alkoxylated polyol.

The linked esterified alkoxylated polyols of this invention may be used as partial or total (100%) replacements for conventional lipids in any edible fat-containing food composition. The amount of the fat mimetic employed is sufficient to effectively reduce the available calories of the food composition as compared to a food composition prepared using an equivalent amount (weight or volume) of a conventional fully digestible triglyceride lipid alone. Preferably, at least about 10 percent (more preferably, at least about 25 percent by weight) of the total fat component of the food composition is comprised of the linked esterified alkoxylated polyol.

The triglyceride lipid admixed with the linked esterified alkoxylated polyol may be any of the known edible fatty acid triglycerides available from natural or synthetic sources. These edible fatty acid triglycerides include, but are not limited to, fats and oils such as tallow, soybean oil, cottonseed oil, coconut oil, palm kernel oil, corn oil, fish oil, lard, butterfat, olive oil, palm oil, peanut oil, safflower seed oil, cocoa butter, sesame seed oil, rapeseed oil (both high and low erucic acid varieties), sunflower seed oil, as well as fully or partially hydrogenated derivatives and mixtures of these triglycerides. While the linked esterified alkoxylated polyol may be combined in any portion with the triglyceride lipid, weight ratios of from 5:95 to 95:5 are particularly advantageous. The triglyceride lipid may be selected so as to impart a desirable caloric content, flavor, aroma, mouth feel, thermal stability, viscosity, rheology (Newtonian or non-Newtonian) or other property to the blend and to the final food composition.

The physical, organoleptic, and physiological properties and characteristics of the linked esterified alkoxylated polyols of this invention may be controlled as desired by varying the identities and relative proportions of the polyols, mono-epoxides, polyepoxide-functionalized polyether glycols, and fatty acid entities incorporated therein. The composition of the linked esterified alkoxylated polyols may thus be readily altered so as to render the fat substitute completely liquid, completely solid, or partially liquid and partially solid at room temperature (i.e., the solid fat index may range from 0 to 100%).

In certain embodiments of the invention (for example, where the linked esterified alkoxylated polyol comprises at least 50% by weight of the fat component present in a food product), the linked esterified alkoxylated polyol preferably has a solid fat index as measured by dilatometry of from 0 to a maximum of 50 at body temperature (37° C.) to provide a pleasant creamy or smooth (i.e., non-waxy) consistency and texture in the food product.

The fat substitute of this invention can replace, in full or in part, a triglyceride lipid in a cooking oil, frying oil, salad oil, or shortening, for example. Additional uses include combining the linked esterified alkoxylated polyol with other foodstuff ingredients to form food compositions such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels), fried foods (fried poultry, fritters, fried pies, fried vegetables such as french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies and confectioneries (especially those normally containing fatty ingredients such as chocolate or peanut butter), soups, and dry baking mixes (for muffins, cakes, pancakes, waffles, brownies, and the like). Owing to the fat-like properties and stability of the linked esterified alkoxylated polyols, minimum reformulation of standard food compositions will generally be required. The viscosity, melting profile, yield point, hardness, thixotropic area, liquid/solid stability, solid fat index, rheology, plasticity, and other physical properties of the linked esterified alkoxylated polyol are preferably selected such that they mimic as closely as possible the analogous properties (other than available caloric value) of the conventional triglyceride being replaced.

Illustrative ingredients (including both fatty food ingredients and non-fat food ingredients which may be used in combination with the fat mimetics of this invention include carbohydrates (flour, starches, sugars, celluloses), edible lipids (triglycerides), proteins (from animal or vegetable sources), vitamins, (including, but not limited to, fat soluble vitamins such as vitamin A, vitamin D, vitamin E and vitamin K), antioxidants, emulsifiers (including, but not limited to, the emulsifiers listed as approved for food use in the United States Code of Federal Regulations), thickeners, preservatives, colorants, flavors, fragrances, sugar substitutes (saccharin, aspartame, sucralose, cyclamates, and the like), other fat substitutes or fat mimetics (for example, sucrose polyester, non-linked esterified alkoxylated polyols such as esterified propoxylated glycerin, or caprenin), bulking agents such as polydextrose, dietary fibers, water, milk, spices, eggs, and the like. Oil-in-water or water-in-oil emulsions can be readily prepared by combining water, the linked esterified alkoxylated polyol, and (optionally) other ingredients such as emulsifiers. The linked esterified alkoxylated polyols of this invention are particularly suitable for the preparation of food compositions requiring exposure to elevated temperatures. Unlike other proposed fat substitutes such as proteinaceous macrocolloids or certain polysaccharide-based substances requiring water to render them fat-like in texture, the fat mimetics of this invention are thermally stable and do not readily decompose or lose their fat-like properties when heated. The fat mimetics thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crisping).

From the foregoing description, one skilled in the art can readily ascertain the essential characteristics of this invention and make various changes and modifications of the invention to adapt it to various usages, conditions, and embodiments.

The following examples further illustrate the compositions of this invention, but are not limitative of the invention in any manner whatsoever.

EXAMPLE 1

This example demonstrates the preparation of a linked esterified alkoxylated polyol fat substitute in accordance with the invention.

Glycerin (921 parts) is heated with 80 parts of aqueous 85% potassium hydroxide solution at 110° C. and 10mm pressure in a stainless steel stirred autoclave equipped with a dry ice trap for water removal until no further water is being evolved. The reactor is pressurized with nitrogen and cooled to 92° C. Propylene oxide (2320 parts) is added on a pressure demand basis, maintaining a reactor pressure of approximately 55 psi. After propylene oxide addition is completed, heating is continued for another 5 hours or until at least 99% of the propylene oxide has reacted. The reactor is then cooled and purged with nitrogen to provide a propoxylated glycerin containing approximately 4 equivalents of propylene oxide per equivalent of glycerin. Potassium is removed from the propoxylated glycerin by heating at 120° C. for 2 hours with 10 weight percent magnesium silicate and then filtering.

The propoxylated glycerin (324.1 parts) is reacted at 150° C. with methyl oleate (593 parts) in the presence of potassium methoxide catalyst (6.0 parts) at 10 mm pressure in a three neck reaction flask equipped with a thermometer and a Dean-Stark distilling head to collect the methanol co-product until at least 98% conversion of the methyl oleate is attained. The product thus obtained is a partially esterified propoxylated glycerin wherein, on average, about 2 hydroxy groups of the propoxylated glycerin have been esterified with oleic acid. Polypropylene glycol diglycidyl ether (320 parts; available from Aldrich Chemical Company) having an average of about 7 ring-opened propylene oxide units per molecule is then added to the reaction flask and heating continued at 150° C. until essentially complete conversion of the polypropylene glycol diglycidyl ether is achieved. The reaction product is heated for 5 hours at 110° C. with 5% by weight magnesium silicate and then filtered to remove the potassium catalyst. The linked esterified alkoxylated polyol thus obtained is subjected to vacuum steam distillation at 10mm pressure at 200° C. to yield a purified material useful as a fat substitute in the preparation of reduced calorie food products.

EXAMPLE 2

This example demonstrates the preparation of a linked esterified alkoxylated polyol fat substitute in accordance with the invention from a diglyceride.

Glycerol distearate (625 parts) is reacted with 984.5 parts of a tetraglycidyl ether of propoxylated pentaerythritol (wherein the propoxylated glycerin contains an average of about 12 ring-opened propylene oxide molecules per equivalent of pentaerythritol) in the presence of sodium metal (0.5% by weight) at 125° C. until essentially complete tetraglycidyl ether conversion is observed. The hydroxy groups generated by ring-opening of the glycidyl groups on the tetraglycidyl ether are then esterified with soybean fatty acid methyl esters (10% molar excess relative to the hydroxy group concentration) at 200° C. and 10 mm pressure until substantially complete conversion of the hydroxy groups is realized. The linked esterified alkoxylated polyol product thus obtained is purified using the procedures described on Example 1 to remove catalyst and excess fatty acid.

EXAMPLE 3

This example illustrates the utility of the linked esterified alkoxylated polyols of this invention as fat substitutes in food products having a reduced level of available calories as compared to analogous products prepared using natural triglycerides exclusively. Sugar cookies may be prepared by blending:

| Ingredient | Parts By Weight |
| --- | --- |
| Sugar | 231 |
| Linked Esterified Alkoxylated Polyol (Example 1) | 86 |
| Corn Oil | 28 |
| Salt | 3.7 |
| Sodium Bicarbonate | 4.4 |
| Water | 37.4 |
| Dextrose Solution (5.9% wt/wt) | 58.7 |
| Flour | 391 |

All of the ingredients are creamed together. The dough so formed may be extruded, cut into thin uniform slices (⅛-¼" thick), and baked at 350° C. until browned and crisp (about 10–12 minutes).

We claim:

1. A linked esterified alkoxylated polyol useful as a reduced calorie fat substitute comprised of at least one polyether glycol linking segment, at least two polyol segments, wherein each polyol segment is connected to a polyether glycol linking segment either directly or through an unesterified oxyalkylene segment, and at least one fatty substituent selected from fatty acid ester groups and fatty acid-esterified oxyalkylene segments attached to a polyol segment.

2. The linked esterified alkoxylated polyol of claim 1 wherein each polyether glycol linking segment bears at least two pendant groups selected from hydroxy groups, fatty acid ester groups, hydroxy-terminated oxyalkylene segments, or fatty acid-esterified oxyalkylene segments.

3. The linked esterified alkoxylated polyol of claim 1 wherein each polyether glycol linking segment has the general structure

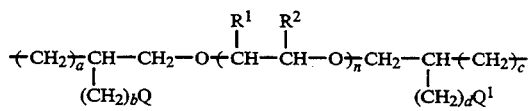

wherein n is an integer of from 1 to 40, Q and $Q^1$ are the same or different and are independently selected from hydroxy groups, fatty acid ester groups, hydroxy-terminated oxyalkylene segments, and fatty acid-esterified oxyalkylene segments, a and b are different and are 0 or 1, c and d are different and are 0 or 1, and $R^1$ and $R^2$ are the same or different and are selected from hydrogen and $C_1$–$C_6$ alkyl.

4. The linked esterified alkoxylated polyol of claim 1 wherein each polyether glycol linking segment is derived from a diepoxide compound having the general structure

wherein n is an integer of from 1 to 40 and AO is selected from oxyethylene, oxypropylene, oxybutylene, and combinations thereof.

5. The linked esterified alkoxylated polyol of claim 1 wherein the polyether glycol linking segment is derived from a polyether glycol bearing from 2 to 8 epoxide functional groups.

6. The linked esterified alkoxylated polyol of claim 5 wherein said polyether glycol is obtained by ring-opening polymerization of ethylene oxide, propylene oxide, 1,2-butene oxide, or a mixture thereof.

7. The linked esterified alkoxylated polyol of claim 1 wherein the polyol segments are derived from an aliphatic polyol having from 3 to 8 hydroxyl groups.

8. The linked esterified alkoxylated polyol of claim 1 wherein the polyol segments are derived from a polyol selected from the group consisting of $C_3$–$C_{12}$ aliphatic triols, $C_4$–$C_{12}$ aliphatic tetrols, $C_5$–$C_8$ sugar alcohols, monosaccharides, disaccharides, alkyl glycosides, and glycerol oligomers.

9. The linked esterified alkoxylated polyol of claim 1 wherein the unesterified oxyalkylene segment has the general structure

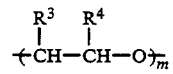

wherein m is an integer of from 1 to 40 and $R^3$ and $R^4$ are the same or different and are independently selected from hydrogen and $C_1$–$C_6$ alkyl.

10. The linked esterified alkoxylated polyol of claim 1 wherein the unesterified oxyalkylene segment is derived from an epoxide selected from ethylene oxide, propylene oxide, 1,2-butene oxide, and mixtures thereof.

11. The linked esterified alkoxylated polyol of claim 1 wherein the fatty substituent has the general structure

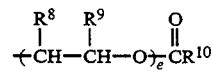

wherein $R^8$ and $R^9$ are the same or different and are independently selected from hydrogen and $C_1$–$C_6$ alkyl, $R^{10}$ is a $C_5$–$C_{23}$ hydrocarbyl group, and e is zero or an integer of from 1 to 40.

12. The linked esterified alkoxylated polyol of claim 11 wherein

is derived from a $C_6$–$C_{24}$ fatty acid entity.

13. The linked esterified alkoxylated polyol of claim 11 wherein the fatty substituent is obtained by ring-opening of an epoxide selected from ethylene oxide, propylene oxide, 1,2-butene oxide, and mixtures thereof and esterifying the ring-opened epoxide with a $C_6$-$C_{24}$ fatty acid, fatty acid ester, fatty acid halide, or fatty acid anhydride.

14. The linked esterified alkoxylated polyol of claim 1 comprising from 2 to 4 polyol segments.

15. The linked esterified alkoxylated polyol of claim 1 wherein the molecular weight of the linked esterified alkoxylated polyol is from 750 to 6000.

16. A linked esterified alkoxylated polyol useful as a reduced calorie fat substitute having a molecular weight of from 750 to 6000 and comprised of
    (a) at least one polyether glycol linking segment having the general structure

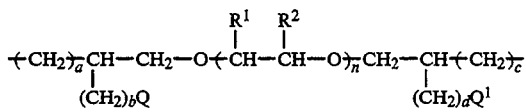

wherein n is an integer of from 1 to 20, Q and $Q^1$ are the same or different and are independently selected from hydroxy groups, fatty acid ester groups, hydroxy-terminated oxyalkylene segments, and fatty acid-esterified oxyalkylene segments, a and b are different and are 0 or 1, c and d are different and are 0 or 1, and $R^1$ and $R^2$ are the same or different and are selected from hydrogen and $C_1$-$C_6$ alkyl;
    (b) from two to four polyol segments derived from an aliphatic polyol having from 3 to 8 hydroxyl groups, wherein each polyol segment is connected to a polyether glycol linking segment either directly or through an unesterified oxyalkylene segment having the general structure

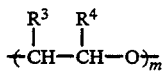

wherein m is an integer of from 1 to 20 and $R^3$ and $R^4$ are the same or different and are selected from hydrogen and $C_1$-$C_6$ alkyl; and
    (c) at least one fatty substituent attached to a polyol segment having the general structure

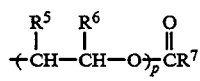

wherein $R^5$ and $R^6$ are the same or different and are independently selected from hydrogen and $C_1$-$C_6$ alkyl, $R^7$ is a $C_5$-$C_{23}$ hydrocarbyl group, and p is zero or an integer of from 1 to 20, wherein the number of polyether glycol linking segments is one less than the number of polyol segments and the number of fatty substituents is at least equal to the number of polyol segments.

17. The linked esterified alkoxylated polyol of claim 16 wherein at least one of $R^1$ or $R^2$ is hydrogen and the other group is hydrogen, methyl or ethyl.

18. The linked esterified alkoxylated polyol of claim 16 wherein the aliphatic polyol is glycerin.

19. The linked esterified alkoxylated polyol of claim 16 wherein at least one of $R^3$ or $R^4$ is hydrogen and the other group is hydrogen, methyl, or ethyl.

20. The linked esterified alkoxylated polyol of claim 16 wherein at least one of $R^5$ or $R^6$ is hydrogen and the other group is hydrogen, methyl, or ethyl.

21. The linked esterified alkoxylated polyol of claim 16 wherein $R^1$ and $R^2$ are different and are hydrogen or methyl, $R^3$ or $R^4$ are different and are hydrogen or methyl, and $R^5$ and $R^6$ are different and are hydrogen or methyl.

22. A fat component useful for preparing a reduced calorie food product, said fat component comprising an edible triglyceride and a linked esterified alkoxylated polyol comprised of at least one polyether glycol linking segment, at least two polyol segments, wherein each polyol segment is connected to a polyether glycol linking segment either directly or through an unesterified oxyalkylene segment, and at least one fatty substituent selected from fatty acid ester groups and fatty acid-esterified oxyalkylene segments attached to a polyol segment.

23. A reduced calorie food product comprised of a fat component, said fat component comprising a linked esterified alkoxylated polyol comprised of at least one polyether glycol linking segment, at least two polyol segments, wherein each polyol segment is connected to a polyether glycol linking segment either directly or through an unesterified oxyalkylene segment, and at least one fatty substituent selected from fatty acid ester groups and fatty acid-esterified oxyalkylene segment attached to a polyol segment.

24. The reduced calorie food product of claim 23 additionally comprising at least one non-fat food ingredient.

25. A linked esterified alkoxylated polyol useful as a reduced calorie fat substitute comprising a polyether glycol linking segment, a first polyol segment attached to the polyether glycol linking segment either directly or through a first unesterified oxyalkylene segment, a second polyol segment attached to the polyether glycol linking segment either directly or through a second unesterified oxyalkylene segment, a first fatty substituent selected from fatty acid ester groups and fatty acid-esterified oxyalkylene segments attached to the first polyol segment, a second fatty substituent selected from fatty acid ester groups and fatty acid-esterified oxyalkylene segments attached to the first polyol segment, a third fatty substituent selected from fatty acid ester groups and fatty acid-esterified oxyalkylene segments attached to the second polyol segment, and a fourth fatty substituent selected from fatty acid ester groups and fatty acid-esterified oxyalkylene segments attached to the second polyol segment.

* * * * *